US00PP10271P

United States Patent [19]

Brown

[11] Patent Number: Plant 10,271

[45] Date of Patent: Mar. 3, 1998

[54] AGLAONEMA PLANT NAMED 'GREEN LADY'

[75] Inventor: B. Frank Brown, Valkaria, Fla.

[73] Assignee: Sunshine Foliage World, Zolfo Springs, Fla.

[21] Appl. No.: 751,958

[22] Filed: Nov. 19, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Assistant Examiner*—Elizabeth C. Kemmerer

*Attorney, Agent, or Firm*—C. A. Whealy

[57] ABSTRACT

A new and distinct cultivar of Aglaonema named 'Green Lady' particularly characterized by its intermediate, dense, compact and freely branching plant habit; dark green leaves with silver green chevron-shaped markings; rapid growth rate; and resistance to diseases common to Aglaonema.

2 Drawing Sheets

The present invention relates to a new and distinct cultivar of Aglaonema plant, botanically known as *Aglaonema hybrida*, and hereinafter referred to by the cultivar name Green Lady.

The new cultivar is a product of a planned breeding program conducted by the inventor in Valkaria, Fla. The new cultivar originated from a cross made by the inventor in March, 1984, between the species *Aglaonema commutatum* as the female, or seed, parent with the species *Aglaonema pictum*. The cultivar Green Lady was discovered and selected by the inventor in April, 1985, as a plant within the progeny of the stated cross in a controlled environment in Valkaria, Fla.

Asexual propagation of the new cultivar by division at Valkaria, Fla., has shown that the unique features of this new Aglaonema plant are stable and reproduced true to type in successive generations of asexual propagation.

The new Aglaonema has not been observed under all possible environmental conditions. The phenotype may vary somewhat with variations in environment such as temperature, light intensity and fertilizer rate, without, however, any variance in genotype. The following observations, measurements and comparisons describe plants grown in Zolfo Springs, Fla., under a polypropylene-covered shadehouse and conditions which closely approximate those used in horticultural practice.

The following traits have been repeatedly observed and are determined to be the unique characteristics of 'Green Lady'. These characteristics in combination distinguish 'Green Lady' as a new and distinct cultivar:

1. Plants of the new Aglaonema are intermediate in size and are freely branching, dense and compact in growth habit.

2. The abaxial leaf surfaces of the new Aglaonema are dark green with silver green chevron-shaped markings. The silver green markings often coalesce to occupy much of the proximal leaf surface. The markings become increasingly sparse near the leaf apex.

3. Plants of the new Aglaonema have a rapid growth rate.

4. Plants of the new Aglaonema are exceptionally resistant to diseases common to Aglaonema.

Plants of the new Aglaonema can be compared to plants of the nonpatented Aglaonema cultivar 'Maria' which have a similar leaf color pattern. However, plants of the new Aglaonema have more and larger leaves with silver green leaf markings, and are more freely branching compared to plants of the cultivar 'Maria'. In addition, plants of the new Aglaonema grow larger and wider than plants of the cultivar 'Maria'.

The accompanying colored photographs illustrate the overall appearance of the new cultivar, showing the colors as true as it is reasonably possible to obtain in colored reproductions of this type.

The first photograph comprises a top perspective view of a typical single plant of 'Green Lady' in a 26-cm container about 16 months after planting a single four-leaf cutting.

The second photograph comprises a close-up view of the abaxial (left) and adaxial (right) surfaces of a mature leaf and illustrates the detail of the leaf color pattern.

Leaf colors in the photographs may appear different from the actual colors due to light reflectance.

In the following description, color references are made to The Royal Horticultural Society Colour Chart except where general terms of ordinary dictionary significance are used.

Botanical Classification: *Aglaonema hybrida* cultivar Green Lady.

Parentage:

*Seed or female parent.*—*Aglaonema commutatum.*

*Pollen or male parent.*—*Aglaonema pictum.*

Propagation: Asexual propagation by division or tissue culture.

Plant Description:

*Plant shape.*—Intermediate in size, outwardly spreading, symmetrical, freely branching, dense and compact in growth habit.

*Growth habit.*—Relatively erect when young, becoming more outwardly spreading as leaves develop.

*Plant size.*—Height: Soil surface to top of leaf canopy: Approximately 50 to 58 cm. Soil surface to junction of the petioles of the last two unrolled leaves: Approximately 19 to 22 cm. Width: Approximately 85 to 89 cm.

*Root description.*—Thick white roots with fine laterals.

*Stem description:*—Upright. Diameter, 5 cm above the soil surface: Approximately 1.5 to 1.7 cm. Internode length, 3 cm above the soil surface: Approximately 1.3 to 2 cm. Color: 147A/147B with areas of 163D.

*Petiole description.*—The following description is based on the fourth expanded leaf from the apex. Growth pattern: The petiole has fleshy edges extending from the midrib that are referred to as wings. Wings extend from the base of the petiole to approximately 2.7 to 5 cm below the base of the leaf. The wings are about 4 mm wide midway from the petiole base to the wing apex. The wing apex is acute. The petiole follows the stem axis but diverges from the axis about 9.8 cm to 11.5 cm from the leaf base, forming a horizontal distance from the vertical axis of the stem to the leaf base of approximately 4 cm to 7.5 cm. Dimensions: The petiole is straight from its base to the tip of the wings, and often curved between the tip of the wings and the base of the leaf. The petiole is approximately 4 mm to 5 mm in diameter midway between the wing apex and the base of the leaf. The petiole is approximately 14.3 cm to 16 cm in length from its base to the base of the leaf. Color: The petiole wings and petiole midrib are 147B sparsely streaked with 147C/147D.

*Axillary breaks.*—There are approximately 18 axillary breaks with at least one leaf expanded. First leaves will show true color and color pattern.

*Leaf description.*—Growth pattern: The leaf is ovate in shape with an acute to acuminate apex and an obtuse base. The leaf margin is entire. The leaf blade is asymmetric with the side of the leaf unrolling first having less surface area than the side unrolling last. The leaf is oriented parallel to the stem axis at the time of full unrolling, changing to approximately 30 to 40 degrees from vertical stem axis as more leaves unroll above it. The midrib is curved downward over the length of the leaf. The leaf blade is flat from the midrib to the margin and often somewhat wavy along the margin. Dimensions: For the pot size and growing time indicated, the largest leaves are approximately 26.5 cm to 28.0 cm long and approximately 8.5 cm to 9.8 cm wide. Average sized leaves are approximately 21.8 cm to 25.3 cm long and approximately 7.8 cm to 8.3 cm wide. The leaf blade is relatively thick and leathery in texture with a glossy surface. Midrib: The midrib is thick and prominent, recessed on the abaxial leaf surface and prominent on the adaxial surface. Primary veins: The primary veins are sunken into the abaxial surface and slightly prominent on the adaxial surface. The primary veins are the same color as the tissue surrounding them. The leaf blade is convex between the primary veins. Pattern: The abaxial leaf surfaces are dark green in base color, with silver green chevron-shaped markings which follow the primary veins. The markings are often composed of two shades of silver green blotches. The leaves are most abundantly marked near their base. The silver green markings often coalesce and occupy much of the proximal leaf surface. The markings become increasingly sparse near the leaf apex. The adaxial leaf surface is entirely medium green. Color: Mature leaf, abaxial surface: Base color: Darker and greener than 147A. Silver green chevon-shaped markings: 191A/194A. Midrib: 147A with streaks of 191A. Mature leaf, adaxial surface: Base color: 147B with very faint markings of 147C which follow the primary veins. Midrib: 147B/147C with streaks of 147C. Newly opened leaf, abaxial surface: Base color: Greener than 147A. Silver green chevon-shaped markings: 191B and 194A/194B. Midrib: Greener than 147A with streaks of 191B. Newly opened leaf, adaxial surface: Base color: 147B/147C with very faint markings of 147C/147D which follow the primary veins. Midrib: 147B/147C.

*Inflorescence.*—Typical of Aglaonema, no commercial significance.

General Observations

Aglaonema 'Green Lady' is a freely branching, intermediate-sized variety having very dense compact growth, and dark green foliage marked with silver green chevron-shaped markings. The silver green markings often coalesce to occupy much of the proximal leaf surface. The markings become increasingly sparse near the leaf apex. Plants of 'Green Lady' have a rapid growth rate and are exceptionally resistant to disease. These characteristics in combination make 'Green Lady' a unique and distinct new cultivar.

It is claimed:

1. A new and distinct cultivar of Aglaonema plant named 'Green Lady', as illustrated and described.

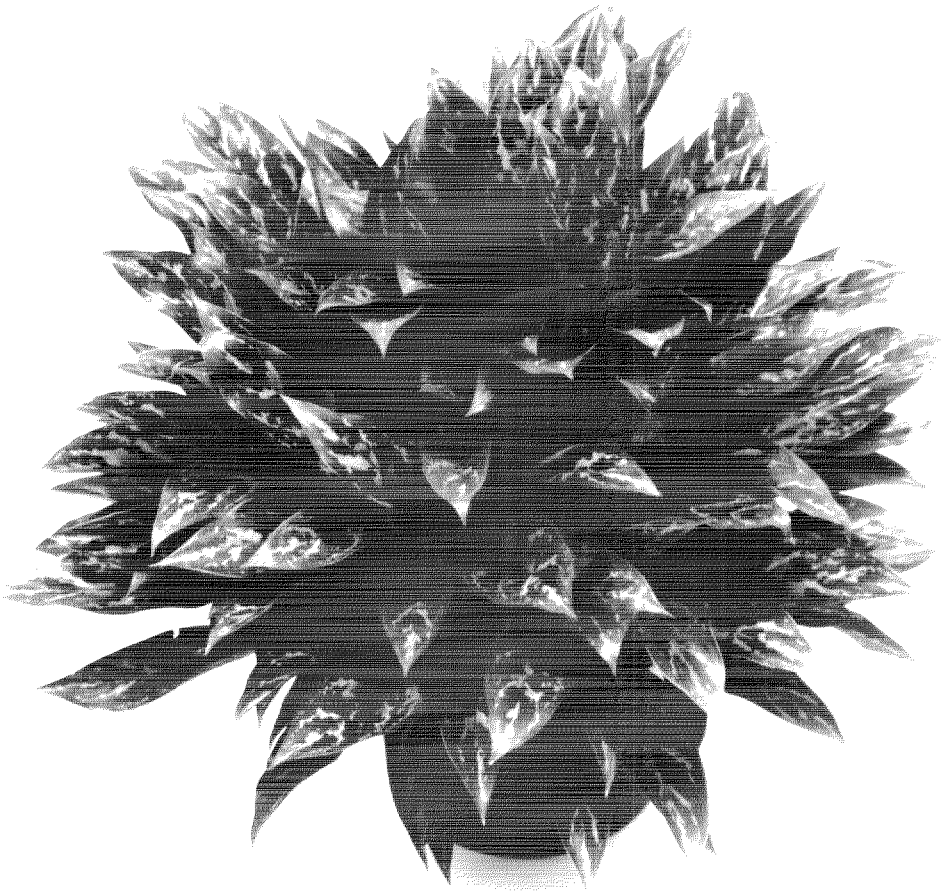

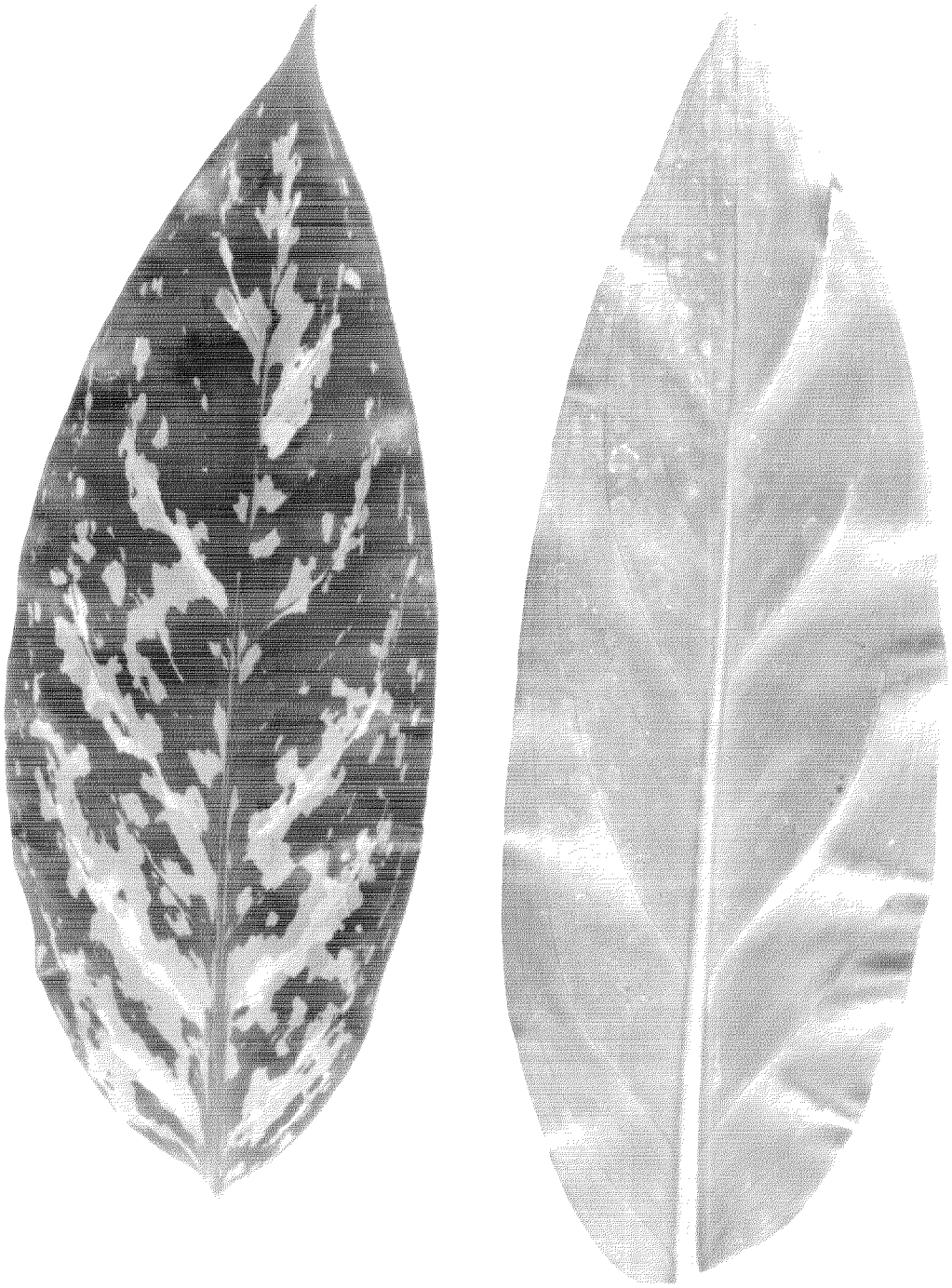

* * * * *